United States Patent [19]
Bloksberg et al.

[11] Patent Number: 5,850,020
[45] Date of Patent: Dec. 15, 1998

[54] MATERIALS AND METHOD FOR THE MODIFICATION OF PLANT LIGNIN CONTENT

[75] Inventors: Leonard N. Bloksberg; Ilkka Havukkala; Alastair Grierson, all of Auckland, New Zealand

[73] Assignees: Genesis Research & Development Corporation, Ltd.; Fletcher Challenge Forests Limited, both of Auckland, New Zealand

[21] Appl. No.: 713,000

[22] Filed: Sep. 11, 1996

[51] Int. Cl.$^6$ .......................... C12N 15/29; C12N 15/82; A01H 4/00; A01H 5/00
[52] U.S. Cl. ................. 800/205; 800/250; 800/DIG. 47; 800/DIG. 51; 435/172.3; 435/320.1; 435/419; 536/23.1; 536/23.2; 536/23.6; 536/24.1; 536/24.2; 536/24.5
[58] Field of Search ..................................... 800/205, 250, 800/DIG. 47, DIG. 51; 435/172.3, 240.4, 320.1, 419; 536/23.1, 23.2, 23.6, 24.1, 24.2, 24.5

[56] References Cited

U.S. PATENT DOCUMENTS

| | | | |
|---|---|---|---|
| 5,122,466 | 6/1992 | Stomp et al. | 435/172.3 |
| 5,451,514 | 9/1995 | Boudet et al. | 435/172.3 |

FOREIGN PATENT DOCUMENTS

| | | | |
|---|---|---|---|
| 4330285 | 11/1992 | Japan | C12N 15/60 |
| 9305160 | 3/1993 | WIPO | C12N 15/54 |
| 9423044 | 10/1994 | WIPO | C12N 15/82 |
| 9527790 | 10/1995 | WIPO | C12N 15/53 |

OTHER PUBLICATIONS

Leonard Nathan Bloksberg, Studies on the Biology of Phenylalanine Ammonia Lyase and Plant Pathogen Interaction, *Genetics*, Abstract iii, Dec. 1991.

D. Palitha Dharmawardhana et al., A β–Glucosidase from Lodgepole Pine Xylem Specific for the Lignin Precursor Coniferin, *Plant Physiol*, 107:331–339, 1995.

G. Schmid et al., Enzymic synthesis of lignin precursors. Purification and properties of UDP glucose: coniferyl–alcohol glucosyltransferase from cambial sap of spruce (Picea abies L.), *Eur J. Biochem* 123:363–70, 1982.

U.N. Dwivedi et al., Modification of lignin biosynthesis in transgenic Nicotiana through expression of an antisense O–methyltransferase gene from Populus, *Plant Molecular Biology* 26:61–71, 1994.

Carolyn Napoli et al., Introduction of a Chimeric Chalcone Synthase Gene into Petunia Results in Reversible Co–Suppression of Homologous Genes in trans, *The Plant Cell 2*: 279–289, Apr. 1990.

Ross Whetten et al., Lignin Biosynthesis, *The Plant Cell* 7:1001–1013, Jul. 1995.

J. Prima–Pettenati et al., Molecular cloning and expression of a *Eucalyptus gunnii* cDNA clone encoding cinnamyl alcohol dehydrogenase, *Plant Mol Biol 21*: 1085–95, 1993.

C. Feuillet et al. Tissue– and cell–specific expression of cinnamyl alcohol dehydrogenase promoter in transgenic poplar plants, *Plant Mol Biol* 27:651–67, 1995.

H. Wengenmayer et al., Enzymic synthesis of lignin precursors. Purification and properties of a cinnamoyl–CoA:NADPH reductase from cell suspension cultures of soybean (Glycinemax), *Eur J. Biochem* 65: 529–536, 1976.

T. Ludertiz et al., Enzymic synthesis of lignin precursors. Comparison of cinnamoyl–CoA reductase and cinnamyl alcohol: NADP+ dehydrogenase from spruce S(Picea abies L.) and Soybean)Glycine max L.), *Eur J. Biochem 119*:115–124, 1981.

F. Sarni et al., Purification and properties of cinnamyl CoA reductase and cinnamyl alcohol dehydrogenase from poplar stems (Populus X euramericana) *Eur J. Biochem 139*: 259–265, 1984.

R.C. Bugos, et al., Characterization of bispecific caffeic acid/5–hydroxyferulic acid O–methyltransferase from aspen, *Phytochemistry 31*:1495–1498, 1992.

C. Hermann et al., Enzymatic synthesis of lignin: Purification to homogeneity of the three O–methyltransferase of tobacco and production of specific antibodies, *Arch Biochem Biophys 253*: 367–376, 1987.

J. Van Doorsselaere et al., One–step purification and characterization of a lignin–specific O–methyltransferase from poplar, *Gene 133*: 213–317, 1993.

R.C. Bugos et al., cDNA cloning, sequence analysis and seasonal expression of lignin–bispecific caffeic acid/5–hydroxyferulic acid O–methyltransferase of aspen, *Plant Mol Biol 17*: 1203–1215, 1991.

P. Collazo et al., Structure and expression of the lignin O–methyltransferase gene from Zea mays L., *Plant Mol Biol 20*: 857–867, 1992.

W. Hosel et al., Characterization of beta–glucosidase isoenzymes possibly involved in lignification from chick pea (Cicer arietinum L.) cell suspension cultures, *Eur J Biochem 84*: 487–492, 1978.

MacKay et al. Genetic analysis of cinnamyl alcohol dehydrogenase in loblolly pine: single gene inheritance, molecular characterization and evolution. Mol. Gen. Genet. (1995) 247: 537–545, Jul. 1995.

*Primary Examiner*—Douglas W. Robinson
*Assistant Examiner*—Thomas Haus
*Attorney, Agent, or Firm*—Janet Sleath; Ann W. Speckman

[57] ABSTRACT

Novel isolated DNA sequences associated with the lignin biosynthetic pathway are provided, together with DNA constructs including such sequences. Methods for the modulation of lignin content in plants are also disclosed, the methods comprising incorporating one or more of the inventive DNA sequences or a sequence complementary to an inventive DNA sequence into the genome of a plant.

39 Claims, 1 Drawing Sheet

MATERIALS AND METHOD FOR THE MODIFICATION OF PLANT LIGNIN CONTENT

TECHNICAL FIELD OF THE INVENTION

This invention relates to the field of modification of lignin content and composition in plants. More particularly, this invention relates to enzymes involved in the lignin biosynthetic pathway and nucleotide sequences encoding such enzymes.

BACKGROUND OF THE INVENTION

Lignin is an insoluble polymer which is primarily responsible for the rigidity of plant stems. Specifically, lignin serves as a matrix around the polysaccharide components of some plant cell walls. The higher the lignin content, the more rigid the plant. For example, tree species synthesize large quantities of lignin, with lignin constituting between 20% to 30% of the dry weight of wood. In addition to providing rigidity, lignin aids in water transport within plants by rendering cell walls hydrophobic and water impermeable. Lignin also plays a role in disease resistance of plants by impeding the penetration and propagation of pathogenic agents.

The high concentration of lignin in trees presents a significant problem in the paper industry wherein considerable resources must be employed to separate lignin from the cellulose fiber needed for the production of paper. Methods typically employed for the removal of lignin are highly energy- and chemical-intensive, resulting in increased costs and increased levels of undesirable waste products. In the U.S. alone, about 20 million tons of lignin are removed from wood per year.

Lignin is largely responsible for the digestibility, or lack thereof, of forage crops, with small increases in plant lignin content resulting in relatively high decreases in digestibility. For example, crops with reduced lignin content provide more efficient forage for cattle, with the yield of milk and meat being higher relative to the amount of forage crop consumed. During normal plant growth, the increase in dry matter content is accompanied by a corresponding decrease in digestibility. When deciding on the optimum time to harvest forage crops, farmers must therefore chose between a high yield of less digestible material and a lower yield of more digestible material.

For some applications, an increase in lignin content is desirable since increasing the lignin content of a plant would lead to increased mechanical strength of wood, changes in its color and increased resistance to rot. Mycorrhizal species composition and abundance may also be favorably manipulated by modifying lignin content and structural composition.

As discussed in detail below, lignin is formed by polymerization of at least three different monolignols which are synthesized in a multistep pathway, each step in the pathway being catalyzed by a different enzyme. It has been shown that manipulation of the number of copies of genes encoding certain enzymes, such as cinnamyl alcohol dehydrogenase (CAD) and caffeic acid 3-O-methyltransferase (COMT) results in modification of the amount of lignin produced; see, for example, U.S. Pat. No. 5,451,514 and PCT publication no. WO 94/23044. Furthermore, it has been shown that antisense expression of sequences encoding CAD in poplar leads to the production of lignin having a modified composition (Grand, C. et al. *Planta (Berl.)* 163:232–237 (1985)).

While DNA sequences encoding some of the enzymes involved in the lignin biosynthetic pathway have been isolated for certain species of plants, genes encoding many of the enzymes in a wide range of plant species have not yet been identified. Thus there remains a need in the art for materials useful in the modification of lignin content and composition in plants and for methods for their use.

SUMMARY OF THE INVENTION

Briefly, the present invention provides isolated DNA sequences obtainable from eucalyptus and pine which encode enzymes involved in the lignin biosynthetic pathway, DNA constructs including such sequences, and methods for the use of such constructs. Transgenic plants having altered lignin content and composition are also provided.

In a first aspect, the present invention provides isolated DNA sequences coding for cinnamyl alcohol dehydrogenase (CAD) isolated from eucalyptus, and for the following enzymes isolated from pine: cinnamate 4-hydroxylase (C4H), coumarate 3-hydroxylase (C3H), phenolase (PNL), O-methyl transferase (OMT), cinnamyl alcohol dehydrogenase (CAD), cinnamoyl-CoA reductase (CCR), phenylalanine ammonia-lyase (PAL), 4-coumarate:CoA ligase (4CL) and peroxidase (POX). In one embodiment, the isolated DNA sequences comprise a nucleotide sequence selected from the group consisting of: (a) sequences recited in SEQ ID NO: 1–13; (b) complements of the sequences recited in SEQ ID NO: 1–13; (c) reverse complements of the sequences recited in SEQ ID NO: 1–13; (d) reverse sequences of the sequences recited in SEQ ID NO: 1–13; and (e) variants of the sequences of (a)–(d).

In another aspect, the invention provides DNA constructs comprising a DNA sequence of the present invention, either alone, in combination with one or more of the inventive sequences or in combination with one or more known DNA sequences; together with transgenic cells comprising such constructs.

In a related aspect, the present invention provides DNA constructs comprising, in the 5'–3' direction, a gene promoter sequence; an open reading frame coding for at least a functional portion of an enzyme encoded by the inventive DNA sequences or variants thereof; and a gene termination sequence. The open reading frame may be orientated in either a sense or antisense direction. DNA constructs comprising a non-coding region of a gene coding for an enzyme encoded by the above DNA sequences or a nucleotide sequence complementary to a non-coding region, together with a gene promoter sequence and a gene termination sequence, are also provided. Preferably, the gene promoter and termination sequences are functional in a host plant. Most preferably, the gene promoter and termination sequences are those of the original enzyme genes but others generally used in the art, such as the Cauliflower Mosaic Virus (CMV) promoter, with or without enhancers, such as the Kozak sequence or Omega enhancer, and *Agrobacterium tumefaciens* nopalin synthase terminator may be usefully employed in the present invention. Tissue-specific promoters may be employed in order to target expression to one or more desired tissues. In a preferred embodiment, the gene promoter sequence provides for transcription in xylem. The DNA construct may further include a marker for the identification of transformed cells.

In a further aspect, transgenic plant cells comprising the DNA constructs of the present invention are provided, together with plants comprising such transgenic cells, and fruits and seeds of such plants.

In yet another aspect, methods for modulating the lignin content and composition of a plant are provided, such methods including stably incorporating into the genome of the plant a DNA construct of the present invention. In a preferred embodiment, the target plant is a woody plant, preferably selected from the group consisting of eucalyptus and pine species, most preferably from the group consisting of *Eucalyptus grandis* and *Pinus radiata*. In a related aspect, a method for producing a plant having altered lignin content is provided, the method comprising transforming a plant cell with a DNA construct of the present invention to provide a transgenic cell, and cultivating the transgenic cell under conditions conducive to regeneration and mature plant growth.

In yet a further aspect, the present invention provides methods for modifying the activity of an enzyme in a plant, comprising stably incorporating into the genome of the plant a DNA construct of the present invention. In a preferred embodiment, the target plant is a woody plant, preferably selected from the group consisting of eucalyptus and pine species, most preferably from the group consisting of *Eucalyptus grandis* and *Pinus radiata*.

The above-mentioned and additional features of the present invention and the manner of obtaining them will become apparent, and the invention will be best understood by reference to the following more detailed description, read in conjunction with the accompanying drawing.

DETAILED DESCRIPTION

Figure 1:
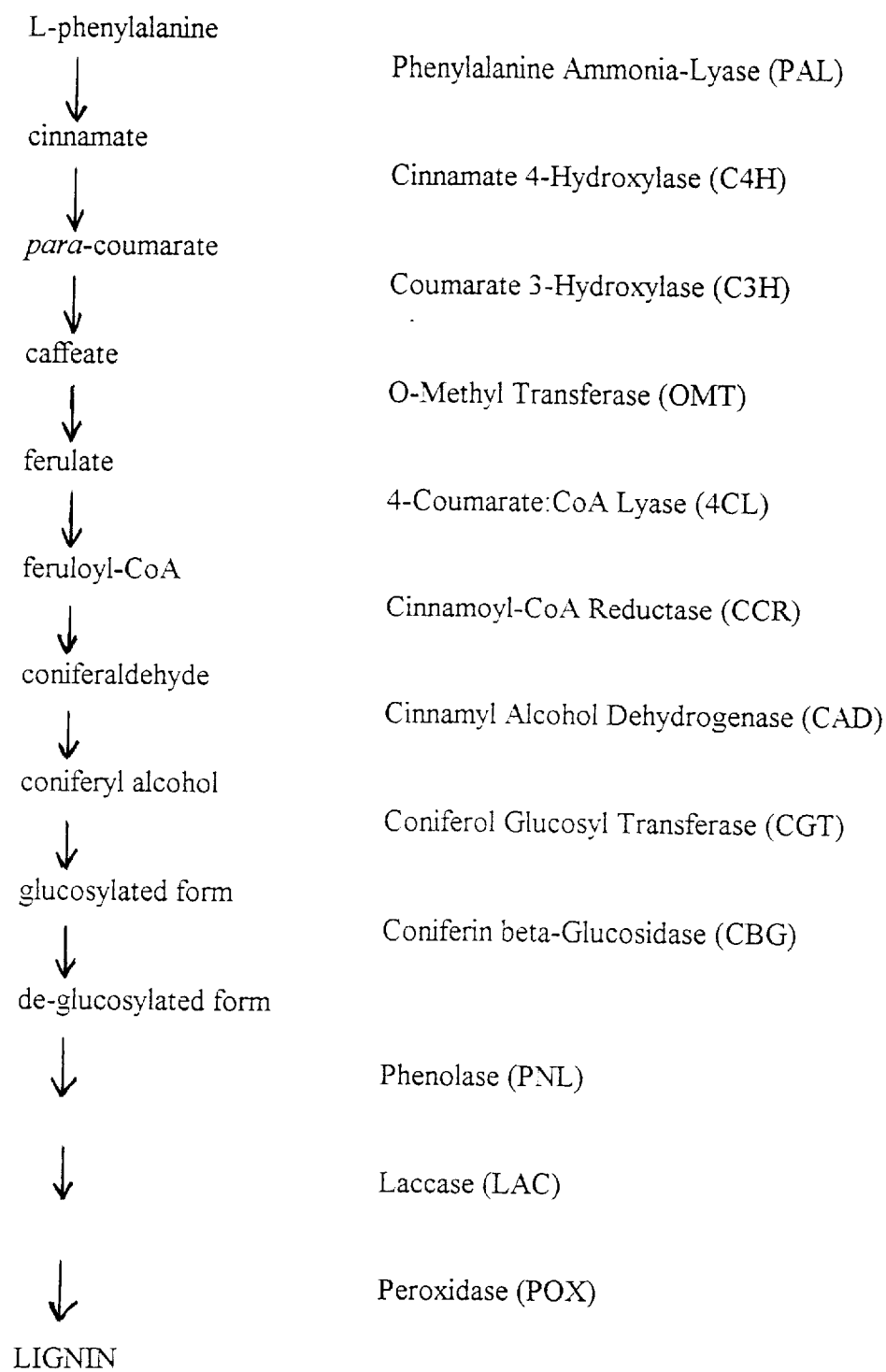
FIG. 1 is a schematic overview of the lignin biosynthetic pathway.

Lignin is formed by polymerization of at least three different monolignols, primarily para-coumaryl alcohol, coniferyl alcohol and sinapyl alcohol. While these three types of lignin subunits are well known, it is possible that slightly different variants of these subunits may be involved in the lignin biosynthetic pathway in various plants. The relative concentration of these residues in lignin varies between different plant species and within species. In addition, the composition of lignin may also vary between different tissues within a specific plant. The three monolignols are derived from phenylalanine in a multistep process and are believed to be polymerized into lignin by a free radical mechanism.

FIG. 1 shows the different steps in the biosynthetic pathway for coniferyl alcohol together with the enzymes responsible for catalyzing each step. para-Coumaryl alcohol and sinapyl alcohol are synthesized by similar pathways. Phenylalanine is first deaminated by phenylalanine ammonia-lyase (PAL) to give cinnamate which is then hydroxylated by cinnamate 4-hydroxylase (C4H) to form p-coumarate. p-Coumarate is hydroxylated by coumarate 3-hydroxylase to give caffeate. The newly added hydroxyl group is then methylated by O-methyl transferase (OMT) to give ferulate which is conjugated to coenzyme A by 4-coumarate:CoA ligase (4CL) to form feruloyl-CoA. Reduction of feruloyl-CoA to coniferaldehyde is catalyzed by cinnamoyl-CoA reductase (CCR). Coniferaldehyde is further reduced by the action of cinnamyl alcohol dehydrogenase (CAD) to give coniferyl alcohol which is then converted into its glucosylated form for export from the cytoplasm to the cell wall by coniferol glucosyl transferase (CGT). Following export, the de-glucosylated form of coniferyl alcohol is obtained by the action of coniferin beta-glucosidase (CBG). Finally, polymerization of the three monolignols to provide lignin is catalyzed by phenolase (PNL), laccase (LAC) and peroxidase (POX). For a more detailed review of the lignin biosynthetic pathway, see: Whetton, R. and Sederoff, R., *The Plant Cell,* 7:1001–1013 (1995).

Quantitative and qualitative modifications in plant lignin content are known to be induced by external factors such as light stimulation, low calcium levels and mechanical stress. Synthesis of new types of lignins, sometimes in tissues not normally lignified, can also be induced by infection with pathogens. In addition to lignin, several other classes of plant products are derived from phenylalanine, including flavonoids, coumarins, stilbenes and benzoic acid derivatives, with the initial steps in the synthesis of all these compounds being the same. Thus modification of the action of PAL, C4H and 4CL may affect the synthesis of other plant products in addition to lignin.

Using the methods and materials of the present invention, the lignin content of a plant can be increased by incorporating additional copies of genes encoding enzymes involved in the lignin biosynthetic pathway into the genome of the target plant. Similarly, a decrease in lignin content can be obtained by transforming the target plant with antisense copies of such genes. In addition, the number of copies of genes encoding for different enzymes in the lignin biosynthetic pathway can be manipulated to modify the relative amount of each monolignol synthesized, thereby leading to the formation of lignin having altered composition. The alteration of lignin composition would be advantageous, for example, in tree processing for paper, and may also be effective in altering the palatability of wood materials to rotting fungi.

In one embodiment, the present invention provides isolated complete or partial DNA sequences encoding, or partially encoding, enzymes involved in the lignin biosynthetic pathway, the DNA sequences being obtainable from eucalyptus and pine. Specifically, the present invention provides isolated DNA sequences encoding the enzyme CAD from *Eucalyptus grandis* (SEQ ID NO: 1) and the enzymes C4H (SEQ ID NO: 2 and 3), C3H (SEQ ID NO: 4), PNL (SEQ ID NO: 5), OMT (SEQ ID NO: 6), CAD (SEQ ID NO: 7), CCR (SEQ ID NO: 8), PAL (SEQ ID NO: 9–11) and 4CL (SEQ ID NO: 12) and POX (SEQ ID NO: 13) from *Pinus radiata,* complements of such isolated DNA sequences, reverse complements of such isolated DNA sequences and reverse sequences of such isolated DNA sequences, together with variants of such sequences. DNA sequences encompassed by the present invention include cDNA, genomic DNA, recombinant DNA and wholly or partially chemically synthesized DNA molecules.

The definition of the terms "complement", "reverse complement" and "reverse sequence", as used herein, is best illustrated by the following example. For the sequence 5'AGGACC3', the complement, reverse complement and reverse sequence are as follows:
complement 3'TCCTGG5'
reverse complement 3'GGTCCT5'
reverse sequence 5'CCAGGA3'.

As used herein, the term "variant" covers any sequence which has at least about a 99% probability of being the same as the inventive sequence. The probability for DNA sequences is measured by FASTA (version 2.0u4, February 1996; Pearson W. R. et al., *Proc. Natl. Acad. Sci.,* 85:2444–2448, 1988), the probability for translated DNA sequences is measured by TBLASTX and that for protein sequences is measured by BLASTP (Altschul, S. F. et al. *J. Mol. Biol.,* 215:403–410, 1990). The term "variants" thus encompasses sequences wherein the probability of finding a match by chance (smallest sum probability) in a database, is less than about 1% as measured by any of the above tests.

The inventive DNA sequences may be isolated by high throuthput sequencing of cDNA libraries prepared from *Eucalyptus grandis* and *Pinus radiata* as described below in Examples 1 and 2. Alternatively, oligonucleotide probes based on the sequences provided in SEQ ID NO: 1–13 can be synthesized and used to identify positive clones in either cDNA or genomic DNA libraries from *Eucalyptus grandis* and *Pinus radiata* by means of hybridization or PCR techniques. Probes can be shorter than the sequences provided herein but should be at least about 10, preferably at least about 15 and most preferably at least about 20 nucleotides in length. Hybridization and PCR techniques suitable for use with such oligonucleotide probes are well known in the art. Positive clones may be analyzed by restriction enzyme digestion, DNA sequencing or the like.

In addition, the DNA sequences of the present invention may be generated by synthetic means using techniques well known in the art. Equipment for automated synthesis of oligonucleotides is commercially available from suppliers such as Applied Biosystems, Inc. (Foster City, Calif.) and may be operated according to the manufacturer's instructions.

In one embodiment, the DNA constructs of the present invention include an open reading frame coding for at least a functional portion of an enzyme encoded by a nucleotide sequence of the present invention or a variant thereof. As used herein, the "functional portion" of an enzyme is that portion which contains the active site essential for affecting the metabolic step, i.e. the portion of the molecule that is capable of binding one or more reactants or is capable of improving or regulating the rate of reaction. The active site may be made up of separate portions present on one or more polypeptide chains and will generally exhibit high substrate specificity. The term "enzyme encoded by a nucleotide sequence" as used herein, includes enzymes encoded by a nucleotide sequence which includes the partial isolated DNA sequences of the present invention.

For applications where amplification of lignin synthesis is desired, the open reading frame is inserted in the DNA construct in a sense orientation, such that transformation of a target plant with the DNA construct will lead to an increase in the number of copies of the gene and therefore an increase in the amount of enzyme. When down-regulation of lignin synthesis is desired, the open reading frame is inserted in the DNA construct in an antisense orientation, such that the RNA produced by transcription of the DNA sequence is complementary to the endogenous MRNA sequence. This, in turn, will result in a decrease in the number of copies of the gene and therefore a decrease in the amount of enzyme. Alternatively, regulation can be achieved by inserting appropriate sequences or subsequences (e.g. DNA or RNA) in ribozyme constructs.

In a second embodiment, the inventive DNA constructs comprise a nucleotide sequence including a non-coding region of a gene coding for an enzyme encoded by a DNA sequence of the present invention, or a nucleotide sequence complementary to such a non-coding region. Examples of non-coding regions which may be usefully employed in such constructs include introns and 5'-non-coding leader sequences. Transformation of a target plant with such a DNA construct may lead to a reduction in the amount of lignin synthesized by the plant by the process of cosuppression, in a manner similar to that discussed, for example, by Napoli et al. (*Plant Cell* 2:279–290, 1990) and de Carvalho Niebel et al. (*Plant Cell* 7:347–358, 1995).

The DNA constructs of the present invention further comprise a gene promoter sequence and a gene termination sequence, operably linked to the DNA sequence to be transcribed, which control expression of the gene. The gene promoter sequence is generally positioned at the 5' end of the DNA sequence to be transcribed, and is employed to initiate transcription of the DNA sequence. Gene promoter sequences are generally found in the 5' non-coding region of a gene but they may exist in introns (Luehrsen, K. R., *Mol. Gen. Genet.* 225:81–93, 1991) or in the coding region, as for example in PAL of tomato (Bloksberg, 1991, Studies on the Biology of Phenylalanine ammonia lyase and plant pathogen interaction. Ph.D. Thesis, Univ. of California, Davis, University Microfilms International order number 9217564). When the construct includes an open reading frame in a sense orientation, the gene promoter sequence also initiates translation of the open reading frame. For DNA constructs comprising either an open reading frame in an antisense orientation or a non-coding region, the gene promoter sequence consists only of a transcription initiation site having a RNA polymerase binding site.

A variety of gene promoter sequences which may be usefully employed in the DNA constructs of the present invention are well known in the art. The promoter gene sequence, and also the gene termination sequence, may be endogenous to the target plant host or may be exogenous, provided the promoter is functional in the target host. For example, the promoter and termination sequences may be from other plant species, plant viruses, bacterial plasmids and the like. Preferably, gene promoter and termination sequences are from the inventive sequences themselves.

Factors influencing the choice of promoter include the desired tissue specificity of the construct, and the timing of transcription and translation. For example, constitutive promoters, such as the 35S Cauliflower Mosaic Virus (CaMV 35S) promoter, will affect the activity of the enzyme in all parts of the plant. Use of a tissue specific promoter will result in production of the desired sense or antisense RNA only in the tissue of interest. With DNA constructs employing inducible gene promoter sequences, the rate of RNA polymerase binding and initiation can be modulated by external stimuli, such as light, heat, anaerobic stress, alteration in nutrient conditions and the like. Temporally regulated promoters can be employed to effect modulation of the rate of RNA polymerase binding and initiation at a specific time during development of a transformed cell. Preferably, the original promoters from the enzyme gene in question, or promoters from a specific tissue-targeted gene in the organism to be transformed, such as eucalyptus or pine are used. Other examples of gene promoters which may be usefully employed in the present invention include, mannopine synthase (mas), octopine synthase (ocs) and those reviewed by Chua et al. (*Science,* 244:174–181, 1989).

The gene termination sequence, which is located 3' to the DNA sequence to be transcribed, may come from the same gene as the gene promoter sequence or may be from a different gene. Many gene termination sequences known in the art may be usefully employed in the present invention, such as the 3' end of the *Agrobacterium tumefaciens* nopaline synthase gene. However, preferred gene terminator sequences are those from the original enzyme gene or from the target species to be transformed.

The DNA constructs of the present invention may also contain a selection marker that is effective in plant cells, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which is usually toxic to plant cells at a moderate concentration (Rogers et al. in *Methods for Plant Molecular Biology,* A. Weissbach and H. Weissbach, eds., Academic Press Inc., San Diego, Calif. (1988)). Alternatively, the presence of the desired construct in transformed cells can be determined by means of other techniques well known in the art, such as Southern and Western blots.

Techniques for operatively linking the components of the inventive DNA constructs are well known in the art and include the use of synthetic linkers containing one or more restriction endonuclease sites as described, for example, by Maniatis et al., (*Molecular Cloning: A Laboratory Manual,* Cold Spring Harbor Laboratories, Cold Spring Harbor, N.Y., 1989). The DNA construct of the present invention may be linked to a vector having at least one replication system, for example, *E. coli,* whereby after each manipulation, the resulting construct can be cloned and sequenced and the correctness of the manipulation determined.

The DNA constructs of the present invention may be used to transform a variety of plants, both monocotyledonous (e.g. grasses, corn, grains, oat, wheat and barley), dicotyledonous (e.g. Arabidopsis, tobacco, legumes, alfalfa, oaks, eucalyptus, maple), and Gymnosperms (e.g. Scots pine (Aronen, Finnish Forest Res. Papers, vol. 595, 1996), white spruce (Ellis et al., Biotechnology 11:94–92, 1993), larch (Huang et al., *In Vitro Cell* 27:201–207, 1991). In a preferred embodiment, the inventive DNA constructs are employed to transform woody plants, herein defined as a tree or shrub whose stem lives for a number of years and increases in diameter each year by the addition of woody tissue. Preferably the target plant is selected from the group consisting of eucalyptus and pine species, most preferably from the group consisting of *Eucalyptus grandis* and *Pinus radiata.* As discussed above, transformation of a plant with a DNA construct including an open reading frame coding for an enzyme encoded by an inventive DNA sequence wherein the open reading frame is orientated in a sense direction will lead to an increase in lignin content of the plant or, in some cases, to a decrease by cosuppression. Transformation of a plant with a DNA construct comprising an open reading frame in an antisense orientation or a non-coding (untranslated) region of a gene will lead to a decrease in the lignin content of the transformed plant.

Techniques for stably incorporating DNA constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by Agrobacterium Ti plasmid technology, as described, for example by Bevan (*Nucl. Acid Res.* 12:8711–8721, 1984). Targets for the introduction of the DNA constructs of the present invention include tissues, such as leaf tissue, disseminated cells, protoplasts, seeds, embryos, meristematic regions; cotyledons, hypocotyls, and the like. The preferred method for transforming eucalyptus and pine is a biolistic method using pollen (see, for example, Aronen 1996, Finnish Forest Res. Papers vol. 595, 53 pp) or easily regenerable embryonic tissues.

Once the cells are transformed, cells having the inventive DNA construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees see Dunstan et al., Somatic embryogenesis in woody plants. In: Thorpe, T. A. ed., 1995: in vitro embryogenesis of plants. Vol. 20 in Current Plant Science and Biotechnology in Agriculture, Chapter 12, pp. 471–540. Specific protocols for the regeneration of spruce are discussed by Roberts et al., (Somatic Embryogenesis of Spruce. In: *Synseed. Applications of synthetic seed to crop improvement.* Redenbaugh, K., ed. CRC Press, Chapter 23, pp. 427–449, 1993). The resulting transformed plants may be reproduced sexually or asexually, using methods well known in the art, to give successive generations of transgenic plants.

As discussed above, the production of RNA in target plant cells can be controlled by choice of the promoter sequence, or by selecting the number of functional copies or the site of integration of the DNA sequences incorporated into the genome of the target plant host. A target plant may be transformed with more than one DNA construct of the present invention, thereby modulating the lignin biosynthetic pathway for the activity of more than one enzyme, affecting enzyme activity in more than one tissue or affecting enzyme activity at more than one expression time. Similarly, a DNA construct may be assembled containing more than one open reading frame coding for an enzyme encoded by a DNA sequence of the present invention or more than one non-coding region of a gene coding for such an enzyme. The DNA sequences of the present inventive may also be employed in combination with other known sequences encoding enzymes involved in the lignin biosynthetic pathway. In this manner, it may be possible to add a lignin biosynthetic pathway to a non-woody plant to produce a new woody plant.

The isolated DNA sequences of the present invention may also be employed as probes to isolate DNA sequences encoding enzymes involved in the lignin synthetic pathway from other plant species, using techniques well known to those of skill in the art.

The following examples are offered by way of illustration and not by way of limitation.

EXAMPLE 1

Isolation and Characterization of cDNA Clones from *Eucalyptus grandis*

Two *Eucalyptus grandis* cDNA expression libraries (one from a mixture of various tissues from a single tree and one from leaves of a single tree) were constructed and screened as follows.

mRNA was extracted from the plant tissue using the protocol of Chang et al. (*Plant Molecular Biology Resorter* 11:113–116 (1993)) with minor modifications. Specifically, samples were dissolved in CPC-RNAXB (100 mM Tris-Cl, pH 8,0; 25 mM EDTA; 2.0M NaCl; 2% CTAB; 2% PVP and 0.05% Spermidine*3 HCl) and extracted with Chloroform:isoamyl alcohol, 24:1. mRNA was precipitated with ethanol and the total RNA preparate was purified using a Poly(A) Quik MRNA Isolation Kit (Stratagene, La Jolla, Calif.). A cDNA expression library was constructed from the purified MRNA by reverse transcriptase synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 µl of sample DNA from the 5 µl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems, Foster City, Calif.) according to the manufacturer's protocol.

DNA sequence for positive clones was obtained using an Applied Biosystems Prism 377 sequencer. cDNA clones were sequenced first from both the 5' end and, in some cases, also from the 3' end. For some clones, internal sequence was obtained using subcloned fragments. Subcloning was performed using standard procedures of restriction mapping and subcloning to pBluescript II SK+vector.

The determined cDNA sequence was compared to known sequences in the EMBL database (release 46, March 1996) using the FASTA algorithm of February 1996 (version 2.0u4) (available on the Internet at the ftp site ftp://ftp.virginia.edu/pub/fasta/). Multiple alignments of redundant sequences were used to build up reliable consensus sequences. Based on similarity to known sequences from other plant species, the isolated DNA sequence (SEQ ID NO: 1) was identified as encoding a CAD enzyme.

EXAMPLE 2

Isolation and Characterization of cDNA Clones from *Pinus radiata* a) Isolation of cDNA clones by high through-put screening

A *Pinus radiata* cDNA expression library was constructed from xylem and screened as described above in Example 1. DNA sequence for positive clones was obtained using forward and reverse primers on an Applied Biosystems Prism 377 sequencer and the determined sequences were compared to known sequences in the database as described above.

Based on similarity to known sequences from other plant species, the isolated DNA sequences were identified as encoding the enzymes C4H (SEQ ID NO: 2 and 3), C3H (SEQ ID NO: 4), PNL (SEQ ID NO: 5), OMT (SEQ ID NO: 6), CAD (SEQ ID NO: 7), CCR (SEQ ID NO: 8), PAL (SEQ ID NO: 9–11) and 4CL (SEQ ID NO: 12).

b) Isolation of cDNA clones by PCR

Two PCR probes, hereinafter referred to as LNB010 and LNB011 (SEQ ID NO: 14 and 15, respectively) were designed based on conserved domains in the following peroxidase sequences previously identified in other species: vanpox, hvupox6, taepox, hvupox1, osapox, ntopox2, ntopox1, lespox, pokpox, luspox, athpox, hrpox, spopox, and tvepox (Genbank accession nos. D11337, M83671, X56011, X58396, X66125, J02979, D11396, X71593, D11102, L07554, M58381, X57564, Z22920, and Z31011, respectively).

RNA was isolated from pine xylem and first strand cDNA was synthesized as described above. This cDNA was subjected to PCR using 4 µM LNB010, 4 µM LNB011, 1×Kogen's buffer, 0.1 mg/ml BSA, 200 mM dNTP, 2 mM $Mg^{2+}$, and 0.1 U/µl of Taq polymerase (Gibco BRL). Conditions were 2 cycles of 2 min at 94° C., 1 min at 55° C. and 1 min at 72° C.; 25 cycles of 1 min at 94° C., 1 min at 55° C., and 1 min at 72° C.; and 18 cycles of 1 min at 94° C., 1 min at 55° C., and 3 min at 72° C. in a Stratagene Robocycler. The gene was re-amplified in the same manner. A band of about 200 bp was purified from a TAE agaorse gel using a Schleicher & Schuell Elu-Quik DNA purification kit and clones into a T-tailed pBluescript vector (Marchuk D. et al., *Nucleic Acids Res.* 19:1154, 1991). Based on similarity to known sequences, the isolated gene (SEQ ID NO: 13) was identified as encoding pine peroxidase (POX).

Although the present invention has been described in some detail by way of illustration and example for purposes of clarity of understanding, changes and modifications can be carried out without departing from the scope of the invention which is intended to be limited only by the scope of the appended claims.

We claim:

1. An isolated DNA sequence comprising a nucleotide sequence selected from the group consisting of:
   (a) sequences recited in SEQ ID NO: 1–6 and 8–13;
   (b) complements of the sequences recited in SEQ ID NO: 1–6 and 8–13;
   (c) reverse complements of the sequences recited in SEQ ID NO: 1–6 and 8–13;
   (d) reverse sequences of the sequences recited in SEQ ID NO: 1–6 and 8–13; and
   (e) sequences having at least about a 99% probability of being the same as a sequence of (a)–(d) as measured by computer algorithm FASTA.

2. A DNA construct comprising a DNA sequence according to claim 1.

3. A transgenic cell comprising a DNA construct according to claim 2.

4. A DNA construct comprising, in the 5'–3' direction:
   (a) a gene promoter sequence;
   (b) at least one open reading frame coding for at least one functional portion of an enzyme encoded by a nucleotide sequence selected from the group consisting of sequences recited in SEQ ID NO: 2–6, 8–13 and sequences having at least about a 99% probability of being the same as a sequence recited in SEQ ID NO: 2–6, 8–13 as measured by computer algorithm FASTA; and
   (c) a gene termination sequence.

5. The DNA construct of claim 4 wherein the open reading frame is in a sense orientation.

6. The DNA construct of claim 4 wherein the open reading frame is in an antisense orientation.

7. The DNA construct of claim 4 wherein the gene promoter sequence and gene termination sequences are functional in a plant host.

8. The DNA construct of claim 4 wherein the gene promoter sequence provides for transcription in xylem.

9. The DNA construct of claim 4 further comprising a marker for identification of transformed cells.

10. A DNA construct comprising, in the 5' to 3' direction:
    (a) a gene promoter sequence;
    (b) at least one non-coding region of a gene coding for an enzyme encoded by a nucleotide sequence selected from the group consisting of sequences recited in SEQ ID NO: 1–6, 8–13 and sequences having at least about a 99% probability of being the same as a sequence recited in SEQ ID NO: 1–6, 8–13 as measured by computer algorithm FASTA; and
    (c) a gene termination sequence.

11. The DNA construct of claim 10 wherein the non-coding region is in a sense orientation.

12. The DNA construct of claim 10 wherein the non-coding region is in an antisense orientation.

13. The DNA construct of claim 10 wherein the gene promoter sequence and gene termination sequences are functional in a plant host.

14. The DNA construct of claim 10 wherein the gene promoter sequence provides for transcription in xylem.

15. A transgenic plant cell comprising a DNA construct, the DNA construct comprising, in the 5'–3' direction:
    (a) a gene promoter sequence;
    (b) at least one open reading frame coding for at least one functional portion of an enzyme encoded by a nucleotide sequence selected from the group consisting of sequences recited in SEQ ID NO: 2–6, 8–13 and sequences having at least about a 99% probability of being the same as a sequence recited in SEQ ID NO: 2–6 8–13 as measured by computer algorithm FASTA; and
    (c) a gene termination sequence.

16. The transgenic plant cell of claim 15 wherein the open reading frame is in a sense orientation.

17. The transgenic plant cell of claim 15 wherein the open reading frame is in an antisense orientation.

18. The transgenic plant cell of claim 15 wherein the DNA construct further comprises a marker for identification of transformed cells.

19. A plant comprising a transgenic plant cell according to claim 15, or fruit or seeds thereof.

20. The plant of claim 19 wherein the plant is a woody plant.

21. The plant of claim 20 wherein the plant is selected from the group consisting of eucalyptus and pine species.

22. A transgenic plant cell comprising a DNA construct, the DNA construct comprising, in the 5'–3' direction:
    (a) a gene promoter sequence;
    (b) at least one non-coding region of a gene coding for an enzyme encoded by a nucleotide sequence selected from the group consisting of sequences recited in SEQ ID NO: 1–6, 8–13 and sequences having at least about a 99% probability of being the same as a sequence recited in SEQ ID NO: 1–6, 8–13 as measured by computer algorithm FASTA; and
    (c) a gene termination sequence.

23. The transgenic plant cell of claim 22 wherein the non-coding region is in a sense orientation.

24. The transgenic plant cell of claim 22 wherein the non-coding region is in an antisense orientation.

25. A plant comprising a transgenic plant cell according to claim 22, or fruit or seeds thereof.

26. The plant of claim 25 wherein the plant is a woody plant.

27. The plant of claim 26 wherein the plant is selected from the group consisting of eucalyptus and pine species.

28. A method for modulating the lignin content of a plant comprising stably incorporating into the genome of the plant a DNA construct comprising, in the 5'–3' direction:
    (a) a gene promoter sequence;
    (b) at least one open reading frame coding for at least one functional portion of an enzyme encoded by a nucleotide sequence selected from the group consisting of sequences recited in SEQ ID NO: 2–6, 8–13 and sequences having at least about a 99% probability of being the same as a sequence recited in SEQ ID NO: 2–6, 8–13 as measured by computer algorithm FASTA; and (c) a gene termination sequence.

29. The method of claim 28 wherein the plant is selected from the group consisting of eucalyptus and pine species.

30. The method of claim 28 wherein the open reading frame is in a sense orientation.

31. The method of claim 28 wherein the open reading frame is in an antisense orientation.

32. A method for producing a plant having altered lignin structure comprising:

(a) transforming a plant cell with a DNA construct comprising, in the 5'–3' direction, a gene promoter sequence, at least one open reading frame coding for at least one functional portion of an enzyme encoded by a nucleotide sequence selected from the group consisting of sequences recited in SEQ ID NO: 2–6 and 8–13 and sequences having at least about a 99% probability of being the same as a sequence recited in SEQ ID NO: 2–6, 8–13 as measured by computer algorithm FASTA, and a gene termination sequence lo provide a transgenic cell;

(b) cultivating the transgenic cell under conditions conducive to regeneration and mature plant growth.

33. The method of claim 32 wherein the open reading frame is in a sense orientation.

34. The method of claim 32 wherein the open reading frame is in an antisense orientation.

35. The method of claim 32 wherein the plant is a woody plant.

36. The method of claim 35 wherein the plant is selected from the group consisting of eucalyptus and pine species.

37. A method of modifying the activity of an enzyme in a plant comprising stably incorporating into the genome of the plant a DNA construct including (a) a gene promoter sequence;

(b) at least one open reading frame coding for at least one functional portion of an enzyme encoded by a nucleotide sequence selected from the group consisting of sequences recited in SEQ ID NO: 2–6 and 8–13 and sequences having at least about a 99% probability of being the same as a sequence recited in SEQ ID NO: 2–6, 8–13 as measured by computer algorithm FASTA; and (c) a gene termination sequence.

38. The method of claim 37 wherein the open reading frame is in a sense orientation.

39. The method of claim 37 wherein the open reading frame is in an antisense orientation.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 535 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
CTTCGCGCTA  CCGCATACTC  CACCACCGCG  TGCAGAAGAT  GAGCTCGGAG  GGTGGGAAGG      60

AGGATTGCCT  CGGTTGGGCT  GCCCGGGACC  TTCTGGGTT   CCTCTCCCCN  TACAAATTCA     120
```

```
CCCGCAGGCC  GTGGGAAGCG  AAGACGTCTC  GATTAAGATC  ACGCACTGTG  GAGTGTGCTA    180

CGCAGATGTG  GCTTGGACTA  GGAATGTGCA  GGGACACTCC  AAGTATCCTC  TGGTGCCGGG    240

GCACGAGATA  GTTGGAATTG  TGAAACAGGT  TGGCTCCAGT  GTCCAACGCT  TCAAAGTTGG    300

CGATCATGTG  GGGGTGGGAA  CTTATGTCAA  TTCATGCAGA  GAGTGCGAGT  ATTGCAATGA    360

CAGGCTAGAA  GTCCAATGTG  AAAAGTCGGT  TATGACTTTT  GATGGAATTG  ATGCAGATGG    420

TACAGTGACA  AAGGGAGGAT  ATTCTAGTCA  CATTGTCGTC  CATGAAAGGT  ATTGCGTCAG    480

GATTCCAGAA  AACTACCCGA  TGGATCTAGC  AGCGCATTGC  TCTGTGCTGG  ATCAC         535
```

( 2 ) INFORMATION FOR SEQ ID NO:2:

( i ) SEQUENCE CHARACTERISTICS:
        ( A ) LENGTH: 671 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
GCGCCTGCAG  GTCGACACTA  GTGGATCCAA  AGAATTCGGC  ACGAGGTTGC  AGGTCGGGGA     60

TGATTTGAAT  CACAGAAACC  TCAGCGATTT  TGCCAAGAAA  TATGGCAAAA  TCTTTCTGCT    120

CAAGATGGGC  CAGAGGAATC  TTGTGGTAGT  TTCATCTCCC  GATCTCGCCA  AGGAGGTCCT    180

GCACACCCAG  GGCGTCGAGT  TTGGGTCTCG  AACCCGGAAC  GTGGTGTTCG  ATATCTTCAC    240

GGGCAAGGGG  CAGGACATGG  TGTTCACCGT  CTATGGAGAT  CACTGGAGAA  AGATGCGCAG    300

GATCATGACT  GTGCCTTTCT  TTACGAATAA  AGTTGTCCAG  CACTACAGAT  CGCGTGGGA     360

AGACGAGATC  AGCCGCGTGG  TCGCGGATGT  GAAATCCCGC  GCCGAGTCTT  CCACCTCGGG    420

CATTGTCATC  CGTAGCGCCT  CCAGCTCATG  ATGTATAATA  TTATGTATAG  GATGATGTTC    480

GACAGGAGAT  TCGAATCCGA  GGACGACCCG  CTTTTCCTCA  AGCTCAAGGC  CCTCAACGGA    540

GAGCGAAGTC  GATTGGCCCA  GAGCTTTGAG  TACAATTATG  GGGATTTCAT  TCCCAGTCTT    600

AGGCCCTTCC  TCAGAGGTTA  TCACAGAATC  TGCAATGAGA  TTAAAGAGAA  ACGGCTCTCT    660

CTTTTCAAGG  A                                                            671
```

( 2 ) INFORMATION FOR SEQ ID NO:3:

( i ) SEQUENCE CHARACTERISTICS:
        ( A ) LENGTH: 940 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
CTTCAGGACA  AGGGAGAGAT  CAATGAGGAT  AATGTTTTGT  ACATCGTTGA  GAACATCAAC     60

GTTGCAGCAA  TTGAGACAAC  GCTGTGGTCG  ATGGAATGGG  GAATAGCGGA  GCTGGTGAAC    120

CACCAGGACA  TTCAGAGCAA  GGTGCGCGCA  GAGCTGGACG  CTGTTCTTGG  ACCAGGCGTG    180

CAGATAACGG  AACCAGACAC  GACAAGGTTG  CCCTACCTTC  AGGCGGTTGT  GAAGGAAACC    240

CTTCGTCTCC  GCATGGCGAT  CCCGTTGCTC  GTCCCCACA   TGAATCTCCA  CGACGCCAAG    300

CTCGGGGGCT  ACGATATTCC  GGCAGAGAGC  AAGATCCTGG  TGAACGCCTG  GTGGTTGGCC    360

AACAACCCCG  CCAACTGGAA  GAACCCCGAG  GAGTTCCGCC  CCGAGCGGTT  CTTCGAGGAG    420

GAGAAGCACA  CCGAAGCCAA  TGGCAACGAC  TTCAAATTCC  TGNCCTTCGG  TGTGGGGAGG    480

AGGAGCTGCC  CGGGAATCAT  TCTGGCGCTG  CTCTCCTCGC  ACTCTCCATC  GGAAGACTTG    540

TTCAGAACTT  CCACCTTCTG  CCGCCGCCCG  GGCAGAGCAA  AGTGGATGTC  ACTGAGAAGG    600
```

| | | | | | | |
|---|---|---|---|---|---|---|
| GCGGGCAATT | CAGCCTTCAC | ATTCTCAACC | ATTCTCTCAT | CGTCGCCAAG | CCCATAGCTT | 660 |
| CTGCTTAATC | CCAACTTGTC | AGTGACTGGT | ATATAAATGC | GCGCACCTGA | ACAAAAAACA | 720 |
| CTCCATCTAT | CATGACTGTG | TGTGCGTGTC | CACTGTCGAG | TCTACTAAGA | GCTCATAGCA | 780 |
| CTTCAAAAGT | TTGCTAGGAT | TTCAATAACA | GACACCGTCA | ATTATGTCAT | GTTTCAATAA | 840 |
| AAGTTTGCAT | AAATTAAATG | ATATTTCAAT | ATACTATTTT | GACTCTCCAC | CAATTGGGGA | 900 |
| ATTTTACTGC | TAAAAAAAAA | AAAAAAAAA | AAAAAAAAA | | | 940 |

( 2 ) INFORMATION FOR SEQ ID NO:4:

( i ) SEQUENCE CHARACTERISTICS:
        ( A ) LENGTH: 949 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

| | | | | | | |
|---|---|---|---|---|---|---|
| NNGCTCNACC | GACGGTGGAC | GGTCCGCTAC | TCAGTAACTG | AGTGGGATCC | CCCGGGCTGA | 60 |
| CAGGCAATTC | GATTTAGCTC | ACTCATTAGG | CACCCCAGGC | TTTACACTTT | ATGCTTCCGG | 120 |
| CTCGTATGTT | GTGTGGAATT | GTGAGCGGAT | AACAATTTCA | CACAGGAAAC | AGCTATGACC | 180 |
| ATGATTACGC | CAAGCGCGCA | ATTAACCCTC | ACTAAGGGA | ACAAAGCTG | GAGCTCCACC | 240 |
| GCGGTGGCGG | CCGCTCTAGA | ACTAGTGGAT | CCAAAGAATT | CGGCACGAGA | CCCAGTGACC | 300 |
| TTCAGGCCTG | AGAGATTTCT | TGAGGAAGAT | GTTGATATTA | AGGGCCATGA | TTACAGGCTA | 360 |
| CTGCCATTGG | TGCAGGGCGC | AGGATCTGCC | CTGGTGCACA | ATTGGGTATT | AATTTAGTTC | 420 |
| AGTCTATGTT | GGGACACCTG | CTTCATCATT | TCGTATGGGC | ACCTCCTGAG | GGAATGAAGG | 480 |
| CAGAAGACAT | AGATCTCACA | GAGAATCCAG | GGCTTGTTAC | TTTCATGGCC | AAGCCTGTGC | 540 |
| AGGCCATTGC | TATTCCTCGA | TTGCCTGATC | ATCTCTACAA | GCGACAGCCA | CTCAATTGAT | 600 |
| CAATTGATCT | GATAGTAAGT | TTGAATTTTG | TTTTGATACA | AAACGAAATA | ACGTGCAGTT | 660 |
| TCTCCTTTTC | CATAGTCAAC | ATGCAGCTTT | CTTTCTCTGA | AGCGCATGCA | GCTTTCTTTC | 720 |
| TCTGAAGCCC | AACTTCTAGC | AAGCAATAAC | TGTATATTTT | AGAACAAATA | CCTATTCCTC | 780 |
| AAATTGAGWA | TTTCTCTGTA | GGGGNNGNTA | ATTGTGCAAT | TTGCAAGNAA | TAGTAAAGTT | 840 |
| TANTTTAGGG | NATTTTAATA | GTCCTANGTA | ANANGNGGNA | ATGNTAGNGG | GCATTNAGAA | 900 |
| ANCCCTAATA | GNTGTTGGNG | GNNGNTAGGN | TTTTTNACCA | AAAAAAAA | | 949 |

( 2 ) INFORMATION FOR SEQ ID NO:5:

( i ) SEQUENCE CHARACTERISTICS:
        ( A ) LENGTH: 959 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

| | | | | | | |
|---|---|---|---|---|---|---|
| GAATTCGGCA | CGAGAAAGCC | CTAGAATTTT | TTCAGCATGC | TATCACAGCC | CCAGCGACAA | 60 |
| CTTTAACTGC | AATAACTGTG | GAAGCGTACA | AAAAGTTTGT | CCTAGTTTCT | CTCATTCAGA | 120 |
| CTGGTCAGGT | TCCAGCATTT | CCAAAATACA | CACCTGCTGT | TGTCCAAAGA | AATTTGAAAT | 180 |
| CTTGCACTCA | GCCCTACATT | GATTTAGCAA | ACAACTACAG | TAGTGGGAAA | ATTTCTGTAT | 240 |
| TGGAAGCTTG | TGTCAACACG | AACACAGAGA | AGTTCAAGAA | TGATAGTAAT | TTGGGGTTAG | 300 |
| TCAAGCAAGT | TTTGTCATCT | CTTTATAAAC | GGAATATTCA | GAGATTGACA | CAGACATATC | 360 |
| TGACCCTCTC | TCTTCAAGAC | ATAGCAAGTA | CGGTACAGTT | GGAGACTGCT | AAGCAGGCTG | 420 |

| | | | | | |
|---|---|---|---|---|---|
| AACTCCATGT | TCTGCAGATG | ATTCAAGATG | GTGAGATTTT | TGCAACCATA | AATCAGAAAG | 480
| ATGGGATGGT | GAGCTTCAAT | GAGGATCCTG | AACAGTACAA | AACATGTCAG | ATGACTGAAT | 540
| ATATAGATAC | TGCAATTCGG | AGAATCATGG | CACTATCAAA | GAAGCTCACC | ACAGTAGATG | 600
| AGCAGATTTC | GTGTGATCAT | TCCTACCTGA | GTAAGGTGGG | GAGAGAGCGT | TCAAGATTTG | 660
| ACATAGATGA | TTTTGATACT | GTTCCCCAGA | AGTTCANAAA | TATGTAACAA | ATGATGTAAA | 720
| TCATCTTCAA | GACTCGCTTA | TATTCATTAC | TTTCTATGTG | AATTGATAGT | CTGTTAACAA | 780
| TAGTACTGTG | GCTGAGTCCA | GAAAGGATCT | CTCGGTATTA | TCACTTGACA | TGCCATCAAA | 840
| AAAATCTCAA | ATTTCTCGAT | GTCTAGTCTT | GATTTTGATT | ATGAATGCGA | CTTTTAGTTG | 900
| TGACATTTGA | GCACCTCGAG | TGAACTACAA | AGTTGCATGT | TAAAAAAAAA | AAAAAAAA | 959

( 2 ) INFORMATION FOR SEQ ID NO:6:

( i ) SEQUENCE CHARACTERISTICS:
        ( A ) LENGTH: 1026 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

| | | | | | |
|---|---|---|---|---|---|
| GAATTCGGCA | CGAGCTTTGA | GGCAACCTAC | ATTCATTGAA | TCCCAGGATT | TCTTCTTGTC | 60
| CAAACAGGTT | TAAGGAAATG | GCAGGCACAA | GTGTTGCTGC | AGCAGAGGTG | AAGGCTCAGA | 120
| CAACCCAAGC | AGAGGAGCCG | GTTAAGGTTG | TCCGCCATCA | AGAAGTGGGA | CACAAAAGTC | 180
| TTTTGCAGAG | CGATGCCCTC | TATCAGTATA | TATTGGAAAC | GAGCGTGTAC | CCTCGTGAGC | 240
| CCGAGCCAAT | GAAGGAGCTC | CGCGAAGTGA | CTGCCAAGCA | TCCCTGGAAC | CTCATGACTA | 300
| CTTCTGCCGA | TGAGGGTCAA | TTTCTGGGCC | TCCTGCTGAA | GCTCATTAAC | GCCAAGAACA | 360
| CCATGGAGAT | TGGGGTGTAC | ACTGGTTACT | CGCTTCTCAG | CACAGCCCTT | GCATTGCCCG | 420
| ATGATGGAAA | GATTCTAGCC | ATGGACATCA | ACAGAGAGAA | CTATGATATC | GGATTGCCTA | 480
| TTATTGAGAA | AGCAGGAGTT | GCCCACAAGA | TTGACTTCAG | AGAGGGCCCT | GCTCTGCCAG | 540
| TTCTGGACGA | ACTGCTTAAG | AATGAGGACA | TGCATGGATC | GTTCGATTTT | GTGTTCGTGG | 600
| ATGCGGACAA | AGACAACTAT | CTAAACTACC | ACAAGCGTCT | GATCGATCTG | GTGAAGGTTG | 660
| GAGGTCTGAT | TGCATATGAC | AACACCCTGT | GGAACGGATC | TGTGGTGGCT | CCACCCGATG | 720
| CTCCCCTGAG | GAAATATGTG | AGATATTACA | GAGATTTCGT | GATGGAGCTA | AACAAGGCCC | 780
| TTGCTGTCGA | TCCCCGCATT | GAGATCAGCC | AAATCCCAGT | CGGTGACGGC | GTCACCCTTT | 840
| GCAGGCGTGT | CTATTGAAAA | CAATCCTTGT | TTCTGCTCGT | CTATTGCAAG | CATAAAGGCT | 900
| CTCTGATTAT | AAGGAGAACG | CTATAATATA | TGGGGTTGAA | GCCATTTGTT | TTGTTTAGTG | 960
| TATTGATAAT | AAAGTAGTAC | AGCATATGCA | AAGTTTGTAT | CAAAAAAAAA | AAAAAAAAA | 1020
| AAAAAA | | | | | | 1026

( 2 ) INFORMATION FOR SEQ ID NO:7:

( i ) SEQUENCE CHARACTERISTICS:
        ( A ) LENGTH: 1454 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

| | | | | | |
|---|---|---|---|---|---|
| GAATTCGGCA | CGAGGCCAAC | TGCAAGCAAT | ACAGTACAAG | AGCCAGACGA | TCGAATCCTG | 60
| TGAAGTGGTT | CTGAAGTGAT | GGGAAGCTTG | GAATCTGAAA | AAACTGTTAC | AGGATATGCA | 120

```
GCTCGGGACT CCAGTGGCCA CTTGTCCCCT TACACTTACA ATCTCAGAAA GAAAGGACCT      180
GAGGATGTAA TTGTAAAGGT CATTTACTGC GGAATCTGCC ACTCTGATTT AGTTCAAATG      240
CGTAATGAAA TGGACATGTC TCATTACCCA ATGGTCCCTG GGCATGAAGT GGTGGGGATT      300
GTAACAGAGA TTGGCAGCGA GGTGAAGAAA TTCAAAGTGG GAGAGCATGT AGGGGTTGGT      360
TGCATTGTTG GGTCCTGTCG CAGTTGCGGT AATTGCAATC AGAGCATGGA ACAATACTGC      420
AGCAAGAGGA TTTGGACCTA CAATGATGTG AACCATGACG GCACACCTAC TCAGGGCGGA      480
TTTGCAAGCA GTATGGTGGT TGATCAGATG TWTGTGGTTC GAATCCCGGA GAATCTTCCT      540
CTGGAACAAG CGGCCCCTCT GTTATGTGCA GGGGTTACAG TTTTCAGCCC AATGAAGCAT      600
TTCGCCATGA CAGAGCCCGG GAAGAAATGT GGGATTTTGG GTTAGGAGG CGTGGGGCAC       660
ATGGGTGTCA AGATTGCCAA AGCCTTTGGA CTCCACGTGA CGGTTATCAG TTCGTCTGAT      720
AAAAAGAAAG AAGAAGCCAT GGAAGTCCTC GGCGCCGATG CTTATCTTGT TAGCAAGGAT      780
ACTGAAAAGA TGATGGAAGC AGCAGAGAGC CTAGATTACA TAATGGACAC CATTCCAGTT      840
GCTCATCCTC TGGAACCATA TCTTGCCCTT CTGAAGACAA ATGGAAAGCT AGTGATGCTG      900
GGCGTTGTTC CAGAGTCGTT GCACTTCGTG ACTCCTCTCT TAATACTTGG GAGAAGGAGC      960
ATAGCTGGAA GTTTCATTGG CAGCATGGAG GAAACACAGG AAACTCTAGA TTTCTGTGCA     1020
GAGAAGAAGG TATCATCGAT GATTGAGGTT GTGGGCCTGG ACTACATCAA CACGGCCATG     1080
GAAAGGTTGG AGAAGAACGA TGTCCGTTAC AGATTTGTGG TGGATGTTGC TAGAAGCAAG     1140
TTGGATAATT AGTCTGCAAT CAATCAATCA GATCAATGCC TGCATGCAAG ATGAATAGAT     1200
CTGGACTAGT AGCTTAACAT GAAAGGGAAA TTAAATTTTT ATTTAGGAAC TCGATACTGG     1260
TTTTTGTTAC TTTAGTTTAG CTTTTGTGAG GTTGAAACAA TTCAGATGTT TTTTTAACTT     1320
GTATATGTAA AGATCAATTT CTCGTGACAG TAAATAATAA TCCAATGTCT TCTGCCAAAT     1380
TAATATATGT ATTCGTATTT TTATATGAAA AAAAAAAAA AAAAAAAAA AAAAAAAAA       1440
AAAAAAAAAA AAAA                                                        1454
```

( 2 ) INFORMATION FOR SEQ ID NO:8:

( i ) SEQUENCE CHARACTERISTICS:
        ( A ) LENGTH: 740 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
GAATTCGGCA CGAGACCATT TCCAGCTAAT ATTGGCATAG CAATTGGTCA TTCTATCTTT       60
GTCAAAGGAG ATCAAACAAA TTTTGAAATT GGACCTAATG GTGTGGAGGC TAGTCAGCTA      120
TACCCAGATG TGAAATATAC CACTGTCGAT GAGTACCTCA GCAAATTTGT GTGAAGTATG      180
CGAGATTCTC TTCCACATGC TTCAGAGATA CATAACAGTT TCAATCAATG TTTGTCCTAG      240
GCATTTGCCA AATTGTGGGT TATAATCCTT CGTAGGTGTT TGGCAGAACA GAACCTCCTG      300
TTTAGTATAG TATGACGAGC TAGGCACTGC AGATCCTTCA CACTTTTCTC TTCCATAAGA      360
AACAAATACT CACCTGTGGT TTGTTTTCTT TCTTTCTGGA ACTTTGGTAT GGCAATAATG      420
TCTTTGGAAA CCGCTTAGTG TGGAATGCTA AGTACTAGTG TCCAGAGTTC TAAGGGAGTT      480
CCAAAATCAT GGCTGATGTG AACTGGTTGT TCCAGAGGGT GTTACAACC AACAGTTGTT       540
CAGTGAATAA TTTTGTTAGA GTGTTTAGAT CCATCTTTAC AAGGCTATTG AGTAAGGTTG      600
GTGTTAGTGA ACGGAATGAT GTCAAATCTT GATGGGCTGA CTGACTCTCT TGTGATGTCA      660
```

-continued

| AATCTTGATG | GATTGTGTCT | TTTTCAATGG | TAAAAAAAAA | AAAAAAAAAA | AAAAAAAAAA | 720 |
| AAAAAAAAAA | AAAAAAAAA  |            |            |            |            | 740 |

( 2 ) INFORMATION FOR SEQ ID NO:9:

( i ) SEQUENCE CHARACTERISTICS:
        ( A ) LENGTH: 624 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

| GAATTCCTGC | AGCCCGGGGG | ATCCACTAGT | TCTAGAGCGG | CCGCCACCGC | GGTGGAGCTC | 60  |
| GCGCGCCTGC | AGGTCGACAC | TAGTGGATCC | AAAGAATTCG | GCACGAGGCC | CGACGGCCAC | 120 |
| TTGTTGGACG | CCATGGAAGC | TCTCCGGAAA | GCCGGGATTC | TGGAACCGTT | TAAACTGCAG | 180 |
| CCCAAGGAAG | GACTGGCTCT | CGTCAACGGC | ACAGCGGTGG | GATCCGCCGT | GGCCGCGTCC | 240 |
| GTCTGTGTTG | ACGCCAACGT | GCTGGGCGTG | CTGGCTGAGA | TTCTGTCTGC | GCTCTTCTGC | 300 |
| GAGGTGATGC | AAGGGAAACC | GGAGTTCGTA | GATCCGTTAA | CCCACCAGTT | GAAGCACCAC | 360 |
| CCAGGGCAGA | TCGAAGCCGC | GGCCGTCATG | GAGTTCCTCC | TCGACGGTAG | CGACTACGTG | 420 |
| AAAGAAGCAG | CGCGGCTTCA | CGAGAAAGAC | CCGTTGAGCA | AACCGAAACA | AGACCGCTAC | 480 |
| GCTCTGCGAA | CATCGCCACA | GTGGTTGGGG | CCTCCGATCG | AAGTCATCCG | CGCTGCYACT | 540 |
| CACTCCATCG | AGCGGGAGAT | CAATTCCGTC | AACGACAATC | CGTTAATCGA | TGTCTCCAGG | 600 |
| GACATGGCTG | TCCACGGCGG | CAAC       |            |            |            | 624 |

( 2 ) INFORMATION FOR SEQ ID NO:10:

( i ) SEQUENCE CHARACTERISTICS:
        ( A ) LENGTH: 278 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

| GAATTCCTGC | AGCCCGGGGG | ATCCACTAGT | TCTAGAGCGG | CCGCCACCGC | GGTGGAGCTC | 60  |
| CAGTACCTGG | CCAACCCCGT | CACGACTCAC | GTCCAGAGCG | CCGAACAACA | CAACCAGGAT | 120 |
| GTCAATTCCC | TCGGCTTGAT | CTCCGCCAGA | AAGACTGCCG | AGGCCGTTGA | GATTTTAAAG | 180 |
| CTGATGTTCG | CTACATATCT | GGTGGCCTTA | TGCCAGGCGA | TCGATCTCCG | GCACCTGGAA | 240 |
| GAAAACATGC | GATCCGTTGT | GAAGCACGTA | GTCTTGCA   |            |            | 278 |

( 2 ) INFORMATION FOR SEQ ID NO:11:

( i ) SEQUENCE CHARACTERISTICS:
        ( A ) LENGTH: 765 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

| GAGCTCCTGC | AAGTCATCGA | TCATCAGCCC | GTTTCTCGT  | ACATCGACGA | TCCCACAAAT | 60  |
| CCATCATACG | CGCTTATGCT | CCAACTCAGA | GAAGTGCTCG | TAGATGAGGC | TCTCAAATCA | 120 |
| TCTTGCCCAG | ACGGGAATGA | CGAATCCGAT | CACAATTTGC | AGCCCGCTGA | GAGCGCTGGA | 180 |
| GCTGCTGGAA | TATTACCCAA | TTGGGTGTTT | AGCAGGATCC | CCATATTTCA | AGAGGAGTTG | 240 |
| AAGGCCCGTT | TAGAGGAAGA | GGTTCCGAAG | GCGAGGGAAC | GATTCGATAA | TGGGGACTTC | 300 |
| CCAATTGCAA | ACAGAATAAA | CAAGTGCAGG | ACATATCCCA | TTTACAGATT | CGTGAGATCA | 360 |

```
GAGTTGGGAA  CCGATTTGCT  AACAGGGCCC  AAGTGGAGAA  GCCCCGGCGA  AGATATAGAA      420

AAGGTATTTG  AGGGCATTTG  CCAAGGGAAA  ATTGGAAACG  TGATCCTCAA  ATGTCTGGAC      480

GCTTGGGGTG  GGTGCGCTGG  ACCATTCACT  CCACGTGCAT  ATCCTGCGTC  TCCTGCAGCG      540

TTCAATGCCT  CATATTGGGC  ATGGTTTGAT  AGCACCAAAT  CACCCTCTGC  AACGAGCGGC      600

AGAGGTTTCT  GGAGCGCCCA  ACAACAACAA  GTTCTTTGAT  TTAACTGACT  CTTAAGCATT      660

CCTAAACAGC  TTGTTCTTCG  CAATAACGAA  TCTTTCATCT  TCGTTACTTT  GTAAAGATG       720

GGGTTCCAAC  AAAATAGAAG  AAATATTTTC  GATCCAAAAA  AAAAA                       765
```

( 2 ) INFORMATION FOR SEQ ID NO:12:

( i ) SEQUENCE CHARACTERISTICS:
        ( A ) LENGTH: 453 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
TGATTATGCG  GATCCTTGGG  CAGGGATACG  GCATGACAGA  AGCAGGCCCG  GTGCTGGCAA       60

TGAACCTAGC  CTTCGCAAAG  AATCCTTTCC  CCGCCAAATC  TGGCTCCTGC  GGAACAGTCG      120

TCCGGAACGC  TCAAATAAAG  ATCCTCGATT  ACAGGAACTG  GCGAGTCTCT  CCCGCACAAT      180

CAAGCCGGCG  AAATCTGCAT  CCGCGGACCC  GAAATAATGA  AGGATATAT   TAACGACCCG      240

GAATCCACGG  CCGCTACAAT  CGATGAAGAA  GGCTGGCTCC  ACACAGGCGA  CGTCGGGTAC      300

ATTGACGATG  ACGAAGAAAT  CTTCATAGTC  GACAGAGTAA  AGGAGATTAT  CAATATAAAG      360

GCTTCCAGGT  GGATCCTGCT  AATCGAATTC  CTGCAGCCCG  GGGGTCCACT  AGTTCTAGAG      420

CGGCCGCCAC  CGCGGTGGAG  CTCCAGCTTT  TGT                                    453
```

( 2 ) INFORMATION FOR SEQ ID NO:13:

( i ) SEQUENCE CHARACTERISTICS:
        ( A ) LENGTH: 278 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
TCTTCGAATT  CTCTTTCACG  ACTGCTTCGT  TAATGGCTGC  GATGGCTCGA  TATTGTTAGA       60

TGATAACTCA  ACGTTCACCG  GAGAAAAGAC  TGCAGGCCCA  AATGTTAATT  CTGCGAGAGG      120

ATTCGACGTA  ATAGACACCA  TCAAAACTCA  AGTTGAGGCA  GCCTGCAGTG  GTGTCGTGTC      180

AGTTGCCGAC  ATTCTCGCCA  TTGCTGCACG  CGATTCAGTC  GTCCAACTGG  GGGGCCCAAC      240

ATGGACGGTA  CTTCTGGGAG  AAAAGACGGA  TCCGATCA                               278
```

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
CTTCGAATTC  WYTTYCAYGA  YTG                                                 23
```

( 2 ) INFORMATION FOR SEQ ID NO:15:

( i ) SEQUENCE CHARACTERISTICS:

-continued (A) LENGTH: 22 base pairs
(B) TYPE: nucleic acid
(C) STRANDEDNESS: single
(D) TOPOLOGY: linear (xi) SEQUENCE DESCRIPTION: SEQ ID NO:15:

GATCGGATCC RTCYYKYCTY CC                                                                 22